United States Patent [19]

Muschler et al.

[11] Patent Number: 5,626,579
[45] Date of Patent: May 6, 1997

[54] BONE TRANSPORT AND LENGTHENING SYSTEM

[75] Inventors: George F. Muschler, Cleveland Heights; Helmuth Kotschi, Strongsville; William A. Smith, Lyndhurst, all of Ohio

[73] Assignee: The Cleveland Clinic Foundation, Cleveland, Ohio

[21] Appl. No.: 495,924

[22] Filed: Jun. 28, 1995

Related U.S. Application Data

[63] Continuation-in-part of Ser. No. 17,622, Feb. 12, 1993, Pat. No. 5,429,638.

[51] Int. Cl.$^6$ .................................................. A61B 17/56
[52] U.S. Cl. ........................................ 606/60; 606/62
[58] Field of Search ........................ 606/60–68, 72–79, 606/86, 87, 88, 102

[56] References Cited

U.S. PATENT DOCUMENTS

| | | |
|---|---|---|
| 3,976,060 | 8/1976 | Hildebrandt et al. . |
| 4,157,715 | 6/1979 | Westerhoff .................. 606/60 |
| 4,576,158 | 3/1986 | Boland . |
| 4,615,338 | 10/1986 | Ilizarov et al. . |
| 4,846,162 | 7/1989 | Moehring . |
| 4,877,019 | 10/1989 | Vives . |
| 4,973,331 | 11/1990 | Pursley et al. . |
| 5,002,543 | 3/1991 | Bradshaw .................. 606/62 |
| 5,034,012 | 7/1991 | Frigg .......................... 606/62 |
| 5,100,404 | 3/1992 | Hayes ......................... 606/62 |
| 5,102,413 | 4/1992 | Podder ........................ 606/62 |
| 5,152,794 | 10/1992 | Davidson . |
| 5,178,137 | 1/1993 | Goor ........................... 602/16 |
| 5,242,448 | 9/1993 | Pettine ......................... 606/102 |
| 5,263,955 | 11/1993 | Baumgart et al. . |
| 5,356,411 | 10/1994 | Spievack . |
| 5,415,660 | 5/1995 | Campbell et al. . |

OTHER PUBLICATIONS

"First Fully Implantable Intramedullary System For Callus Distraction —Medullary Nail with Programmable Drive for Leg Lengthening and Segment Displacement" (A. Betz et al.) (*Der Chirurg— Technische Neuheiten;* pp.605–609; ©1990).

"Standing Straightener with Smart Materials" (*Machine Design;* Feb., 1995).

*Primary Examiner*—Michael A. Brown
*Attorney, Agent, or Firm*—Fay, Sharpe, Beall, Fagan, Minnich & McKee

[57] ABSTRACT

A surgically implantable cable apparatus has a means for securing (32) a first bone segment (12) and a second bone segment (13). A flexible cable (17) is attached at one end relative to one bone segment (25). A flexible non-compressible sheath (15) has a bore (16) for slidably receiving the cable (17). The non-compressible sheath (15) is secured to the securing means (32) at point (40) and transmits a counter-compression force to the bone segment (25). An implantable actuator (36) is connected to the second end (19) of the flexible cable (17) and to the second end of the sheath (15). The implantable actuator (36) is fully implantable subcutaneously. The implantable actuator (36) is responsive to a transcutaneous energy signal and pulls the flexible cable (17) through the sheath (15) in an axial direction. The cable movement is applied to the bone segment (25), either directly or transmitted through an internal fixation device and the bone segment (25) moves a predetermined distance. An energy source (42) generates the transcutaneous energy signal which activates the implantable actuator (36) through an intact skin layer (44). The transcutaneous energy signal is a magnetic field or induced electrical current.

56 Claims, 5 Drawing Sheets

BONE TRANSPORT AND LENGTHENING SYSTEM

This application is a continuation-in-part of U.S. application Ser. No. 08/017,622, filed Feb. 12, 1993, now U.S. Pat. No. 5,429,638.

BACKGROUND OF THE INVENTION

The present invention relates to the art of in vivo bone treatment. It finds particular application to in vivo bone transport and lengthening and will be described with particular reference thereto.

Intercalary defects in long bones may occur as a result of trauma, resection necessitated by tumors or infection, or acute limb lengthening. With appropriate mechanical fixation, these defects may be managed by autogenous bone grafting, segmental allograft reconstruction, or reconstruction using endoprostheses. Autogenous bone grafting has the disadvantage of donor site morbidity including pain, increased blood loss, and surgical scarring. Furthermore, in the case of large defects it may be difficult or impossible to obtain an optimal volume of autogenous bone. While allografting eliminates the problem of adequate quantity, the incidence of complications such as infection, fracture, and non-union is increased. The risk of exposure to HIV or hepatitis is another concern, raised by the use of allogenous material, bone or transfusion blood to treat bleeding.

In 1954, Ilizarov reported that mature bone can be elongated by gradual distraction of a fracture callus and called this process distraction osteogenesis. The application of this technique in the form of bone segment transport or gradual bone lengthening can obviate the need for open bone grafting in many large diaphyseal defects. Ilizarov used external fixation, with wires passing through the limb and bone, and connected to the external frame. However, transfixing wires used in this technique can cause significant complications including wire site infection, bone infection, pain, scarring, and restricted joint motion due to the transfixation of tendons and muscles. These complications are particularly relevant when the Ilizarov device is applied to the femur.

In 1990, Brunner reported that distraction osteogenesis was achievable using intramedullary fixation in sheep tibiae. Brunner's method still relied on the use of an external fixator to provide the force necessary for bone transport. Brunner's work implied that transfixing wires used for internal fixation could potentially be eliminated.

Betz described the use of a telescoping intramedullary rod for distraction osteogenesis. With the Betz device, the patient apparently turned a small knob that protruded from the patient's hip in order to telescopically move the parts relative to one another.

An example of a medullary nail is seen in PCT Application No. WO 91/00065 naming Rainer Baumgart and Augustin Betz as applicants. The Betz device describes an intramedullary nail that has a cavity in which an inner part can slide longitudinally without being able to rotate. The wall of the medullary nail which forms the cavity is traversed on both sides by an elongated hole in the region of the driving-in end. At least one fastening hole aligned flush with the elongated hole is provided in the inner part. When the connecting screws are driven into the spaced fastening holes an osteotomy is located between the connecting screws, the edges of the osteotomy are moved apart as the inner part slides longitudinally, and the slowly widening gap between the edges of the osteotomy becomes filled with bone tissue.

An extension apparatus, especially for osteotomic surgery is the subject of U.S. Pat. No. 3,976,060 issued to Hildebrandt, et al. The Hildebrandt patent describes a bone extension device that is movably supported in an elongated, slender housing. The extension device includes an extension member movably extending out of a housing. A drive is supported within the housing and operatively connected to the extension device. A drive is energized through a source of power which may be either located in the housing itself or it may be an external power source such as a magnetic field. The power source is operatively connected to the drive. A control is supported within the housing to operate the drive through the power source for moving the extension member. A seal is provided to seal the housing so as to provide a surgically implantable structural unit. The power source can be an electric motor and powered by a battery. Reduction gears are disclosed as rotating a threaded spindle which operates a push rod.

U.S. Pat. No. 4,577,715 entitled "Intracorporal Drive to Produce a Continuous Traction or Pressure and Method of Operating Same" was issued to Erhardt Westerhoff. The drive provides an extension unit for extension osteotomy and for a compression unit for pressure osteosynthesis, wherein the driving power is generated by the osmotic pressure between two differentially concentrated solutions separated from each other by a semipermeable diaphragm or membrane. The solution of low concentration can also be substituted by pure solvent.

The Grammont, et al. U.S. Pat. No. 5,074,882 provides a device that includes a nail for gradually lengthening long bones. The apparatus includes outer and inner sliding tubes connected with a double ratchet mechanism. The nail is fixed by its two extremities in the bone and the device is entirely included within the concerned bone, being lengthened post-operatively by maneuvers applied to the patient's limb. Rotation of a second part of the limb with respect to the first part of the limb allows rotation of the ratchet mechanism with lengthening of the device in one direction, and keeping of the gained length in the other direction while returning the neutral axis of the rotation of the device, thereby featuring a dynamization system, and a system to limit the range of rotation of the device.

Betz, Baumgart, and Schweiberer have published a paper in German, describing a bone lengthening nail incorporating telescoping rods, a lead screw to produce lengthening of the rod assembly, and an electric motor incorporated into one of the rods to produce lead screw rotation. Electrical power from an implanted battery, or transmitted through the skin, is finally delivered to the motor through an electronic controller.

The linear implantable distractors of the prior art suffer because of a failure to afford an easy way of operating such an implantable distraction apparatus, with improved patient comfort, and without bacteriological infiltration. Furthermore, the size of the mechanism incorporated into the rod limits applicability to smaller bones.

Various devices have been patented for distractors that are placed externally of the patient's limb. These are referred to often as "Ilizarov-type" distractors, after the Russian inventor Gavriil Ilizarov. As an example, U.S. Pat. No. 4,615,338 entitled "Automatic Compression-Distraction Apparatus" names Gavriil Ilizarov and others as inventors. The '338 patent relates to a drive of a compression-distraction apparatus, comprising a lead screw whose thread is mated with an opening of a ratchet wheel placed in a housing, a pawl interacting with teeth of the wheel and connected to a load bearing element manufactured from an alloy possessing plastic memory. The load bearing element has a rectilinear shape and is essentially a tie rod whose one end is rigidly secured to the housing while the other end is coupled to a resilient member and the pawl, with the load bearing element being further provided with an electric heater connected to the housing. Another external compression distraction apparatus is the subject of U.S. Pat. No. 4,973,331 issued to Pursley, et al. and entitled "Automatic Compression-Distraction, Torsion Method and Apparatus". This is similar to the Illizarov device, with electric motors driving the lead screw.

Spievack, U.S. Pat. No. 5,356,411 provides a bone transporter having a hydraulic cylinder and a piston. A pump 32 and a reservoir 72 provide an implantable supply of saline operating fluid to the hydraulic cylinder through a conduit 26. The pump 32 and reservoir 72 are implanted subcutaneously. An external pump exciting member 82 activates the pump to cause the saline fluid to pass through the conduit 26 into the medullary nail. Pressure from the fluid transports the bone segment. This device suffers from a disadvantage that a foreign fluid is introduced into the patient.

The present invention provides a new and improved surgically implantable traction cable apparatus which has a subcutaneous actuator for in vivo bone transport, bone lengthening or force transmission to a bone segment.

SUMMARY OF THE INVENTION

In accordance with the present invention, a new and improved method and apparatus for in vivo bone transport of a bone segment between a first bone segment and a second bone segment, or lengthening of a bone, is provided. A flexible cable having a first end portion is attached to the bone segment to which force or motion is applied. An implantable flexible, non-compressible sheath having a bore receives the cable within the bore, and through which a counter-compression force is transmitted. A first end of the sheath is secured to a bone, or the internal fixation device. An implantable actuator is connected to a second end portion of the flexible cable and to the second end of the sheath. The implantable actuator is responsive to a transcutaneous energy signal and pulls the flexible cable through the sheath. An energy source generates the transcutaneous energy signal which activates the implantable actuator through an intact skin layer. Motion of the cable within the sheath displaces the attached bone segment a selected dimension per unit of time (e.g., 0.25 mm per actuator cycle), in response to activation of the actuator.

In accordance with a more limited aspect of the present invention, a rod is surgically implanted into the intramedullary canal of the patient's bone, secured to the first bone segment, the second bone segment, or both.

In accordance with a more limited aspect of the present invention, the implantable actuator is located subcutaneously. The actuator includes a tensioning assembly connected to the second end portion of the flexible cable and applies tension to the flexible cable. The actuator is responsive to the transcutaneous energy signal, and upon receiving the transcutaneous energy signal, moves the flexible cable a predetermined distance.

In accordance with a more limited aspect of the present invention, the tensioning assembly includes a cable take-up spool.

In accordance with a more limited aspect of the present invention, the actuator includes magnetically sensitive elements. The energy source includes means for generating a magnetic field as the transcutaneous energy signal. The means for generating includes permanent magnets, electromagnets, or other conventional means of creating the magnetic field. In response to the magnetic field, the magnetically sensitive elements activate the actuator to move the flexible cable.

In accordance with a more limited aspect of the present invention, the actuator includes a gear stage connected to the tensioning assembly.

In accordance with a more limited aspect of the present invention, the actuator includes thermally sensitive elements. The transcutaneous energy signal heats the thermally sensitive elements, using transmitted power, such as electrical energy, ultrasound, or microwaves. The thermally sensitive elements, in response to the heating, activate the actuator to move the flexible cable.

In accordance with a more limited aspect of the present invention, the thermally sensitive elements are fabricated from a shape memory alloy. The shape memory alloy components are configured to cause a rotational motion, as the temperature changes.

In accordance with another aspect of the present invention, a method of in vivo motion of a bone segment between a first bone segment and a second bone segment of a patient's bone is provided. An implant is affixed to the patient's bone. The patient's bone is severed with a cut that defines a gap. The implant is affixed to the bone at separate positions on opposite sides of the gap. At least a portion of the implant is gradually moved a selected dimension per unit of time in response to a transcutaneous energy signal. A flexible force transmitting member extends from the implant to a remote site where the force is applied from.

One advantage of the present invention is that the flexibility of the cable and the sheath reduces the morbidity of the device by allowing it to flex freely with and within the surrounding tissue. The device allows the free movement of muscles and joints, throughout the time when force is applied to the bone segment.

Another advantage of the present invention is that the actuator is fully implantable subcutaneously, which significantly improves patient convenience and comfort. Since the actuator is connected to a flexible cable and sheath, the actuator can be selectively positioned for patient convenience and comfort. The actuator is activated from an external energy source which is removable when not in use. Another advantage of the present invention is the remote location of the actuator, relative to the intramedullary nail, permits the nail diameter to be smaller, fitting in smaller patients, and in a wider range of bones.

Yet another advantage of the present invention is that the actuator is responsive to a transcutaneous energy signal. Following surgical implantation, the integrity of the patient's skin is maintained. Since the skin is not penetrated, discomfort and surgical infection are reduced. Furthermore, there is no need for continuous bandages or wound care. The strength of the driving energy field is lower, as compared to an actuator located deep in the limb, and therefore at a greater distance from the energy source.

Yet another advantage of the present invention is that the apparatus is capable of an in vivo force which can move one bone segment by pushing or pulling with respect to another bone segment, squeezing or holding the bone segments together, or holding the bone segments apart during the time bone healing is completed.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION OF THE PREFERRED EMBODIMENTS

Figures 1A, 1B:
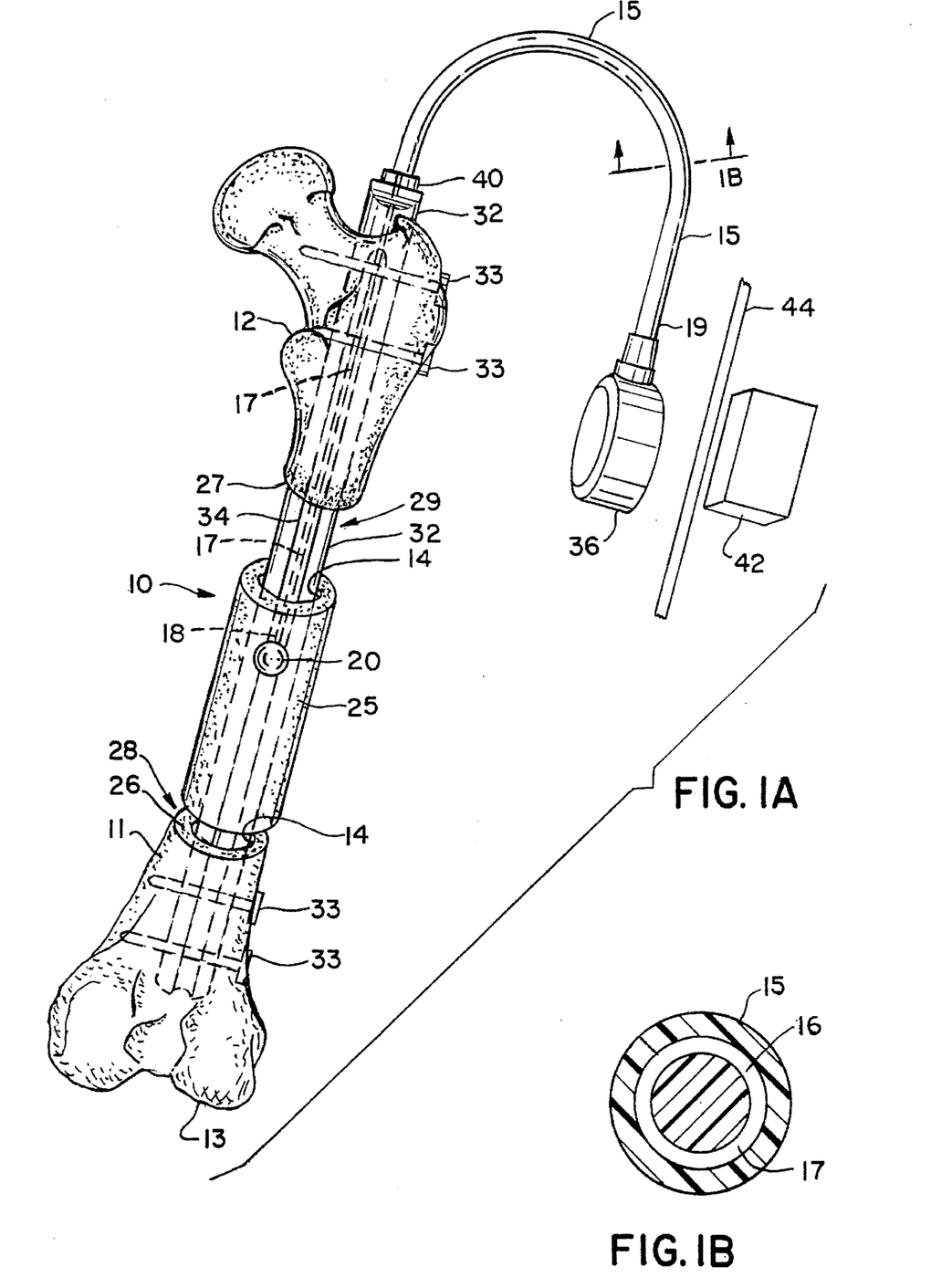
FIG. 1A is a perspective schematic view of the preferred embodiment of the apparatus of the present invention.
FIG. 1B is a cross-sectional view of the cable and sheath assembly of the present invention.
Figure 2:
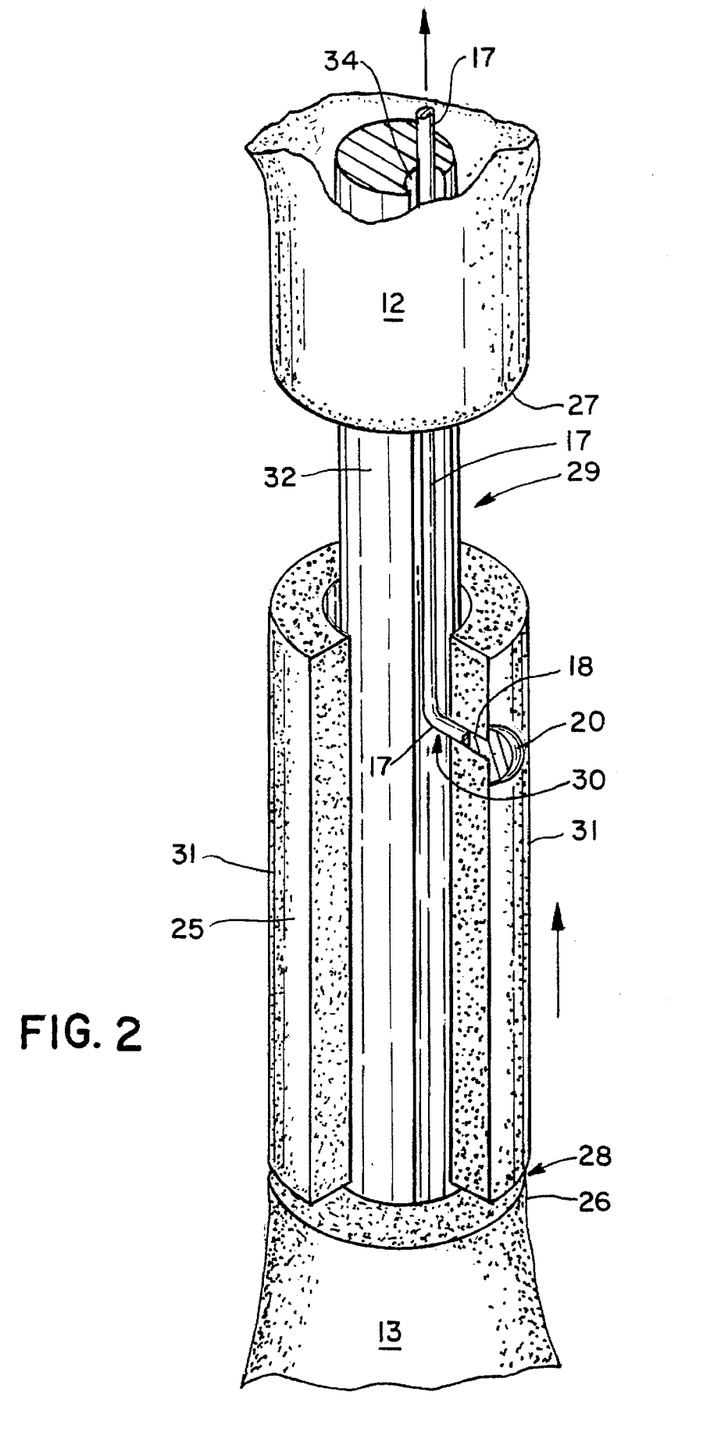
FIG. 2 is a perspective partially cut away fragmentary view of the cable apparatus of the present invention.

With reference to FIGS. 1 and 2, a bone transport and lengthening apparatus 10 is shown in use with a patient's femur 11. The femur 11 is exemplary of a bone that is used with the method and apparatus of the present invention. The femur 11 includes a first end portion 12, a second end portion 13, and intramedullary canal 14.

The intramedullary canal 14 of the femur 11 may be initially prepared proximally and distally (such as by reaming with a reamer) to a desired diameter. A rod 32 (for example, stainless steel) is advanced through the intramedullary canal 14 from the first end portion 12 to the second end portion 13 of femur 11. The rod 32 fixes the positional relationship of the end portions 12 and 13. The rod 32 is held in position, for example, using a plurality of bone screws 33. Each end portion of rod 32 includes multiple transverse openings for accepting bone screws 33 therethrough. The rod 32 includes a longitudinally extending slot 34. A flexible cable 17 tracks the slot 34 during bone transport as shown in FIGS. 1 and 2. Preferably, the flexible cable 17 is a traction cable which mechanically transmits force along its length.

The apparatus 10 includes a flexible outer cable sheath 15 of a preferably non-compressible material such as a coil spring cable of stainless steel, polymeric, or like material. Flexible sheath 15 has an internal bore 16 for accepting the flexible cable 17. The flexible cable 17 is a monofilament cable, or a multifilament cable. The cable 17 is made of metallic or polymeric materials for example.

The cable 17 includes a second end portion 18 and a first end portion 19. The second end portion 18 carries button 20 or other means for attaching the second end 18 of cable 17 to bone segment 25.

With further reference to FIGS. 1 and 2, bone segment 25 is formed by cuts 26, 27 defining gaps 28, 29. The larger gap 29 represents an area where a large bone segment was excised or was absent from the first end portion 12 of femur 11. Gap 29 might also have been purposely created by lengthening the limb at the site of a bone defect or surgical osteotomy. The cut 26 in the small gap 28 represents an osteotomy that was made a selected distance above the second end 13 of femur 11. Following the osteotomy, the bone segment 25 is formed for bone transport. The cable 17 is attached to bone segment 25 using button 20, for example. A hole 30 is formed (such as by drilling) in the bone segment 25 for attachment of the cable 17 to the bone segment 25. The cable 17 is advanced through the hole 30 until the button 20 contacts the outer surface 31 of bone segment 25 as shown in FIG. 2. The free bone segment 25 is then transported proximally along the rod 32 which is implanted in the patient's intramedullary canal. The segment 25 is advanced a desired distance per unit time by pulling the cable 17.

Transportation of the bone segment 25 can begin at a defined time, (for example, within about one week after the osteotomy) and can continue at a desired rate (one millimeter per day for example) and for a number of days until docking occurs. Docking occurs when the bone segment 25 contacts the cut 27 of the femur 11.

An actuator 36 is connected to the first end 19 of cable 17 and produces tension on the cable 17. The sheath 15 affixes to the rod 32 at one end 40 and to the actuator 36 at the other end. The connection 40 allows the compression force transmitted by the cable sheath to be transmitted to the rod. The tension force in the cable 17 is countered by the compression force in the sheath 15. The actuator is implanted subcutaneously. The flexibility of the sheath 15, and selection of an appropriate sheath length and route between bone and subcutaneous actuator allows the actuator to be positioned at any convenient location. The actuator 36 includes elements which are responsive to an external activation device 42. The activation device 42 generates transcutaneous signals which initiate the actuator 36 to move the cable 17 relative to the sheath, thus moving the bone segment 25. The transcutaneous signals include any one of microwaves, radiated energy and other signals as known to those of ordinary skill in the art. The actuator 36 moves the cable 17 continuously or incrementally a predetermined distance each time it is activated. The activation device 42 is generally positioned over the actuator 36 with an intact layer of skin 44 in between.

Surgical implantation of the apparatus proceeds in a series of steps, the order of which is varied to suit the needs of a particular surgeon and patient. In general, a fixation device 32 is attached to the bone segments, creating a fixed or controllable dimensional relationship. The selected bone 11 is severed to produce one or more gaps 26, 27. The cable 17 is fixed to the bone 25 at one end 18, and the other end is put through the sheath 15. One end 19 of the sheath 15 is fixed to the fixation device and the other end is fixed to the actuator 36. The other end 19 of the cable 17 is also fixed to the actuator 36. Upon activation, the actuator 36 gradually distracts the cable 17 and bone 25 post-operatively.

Figures 3A, 3B, 3C:
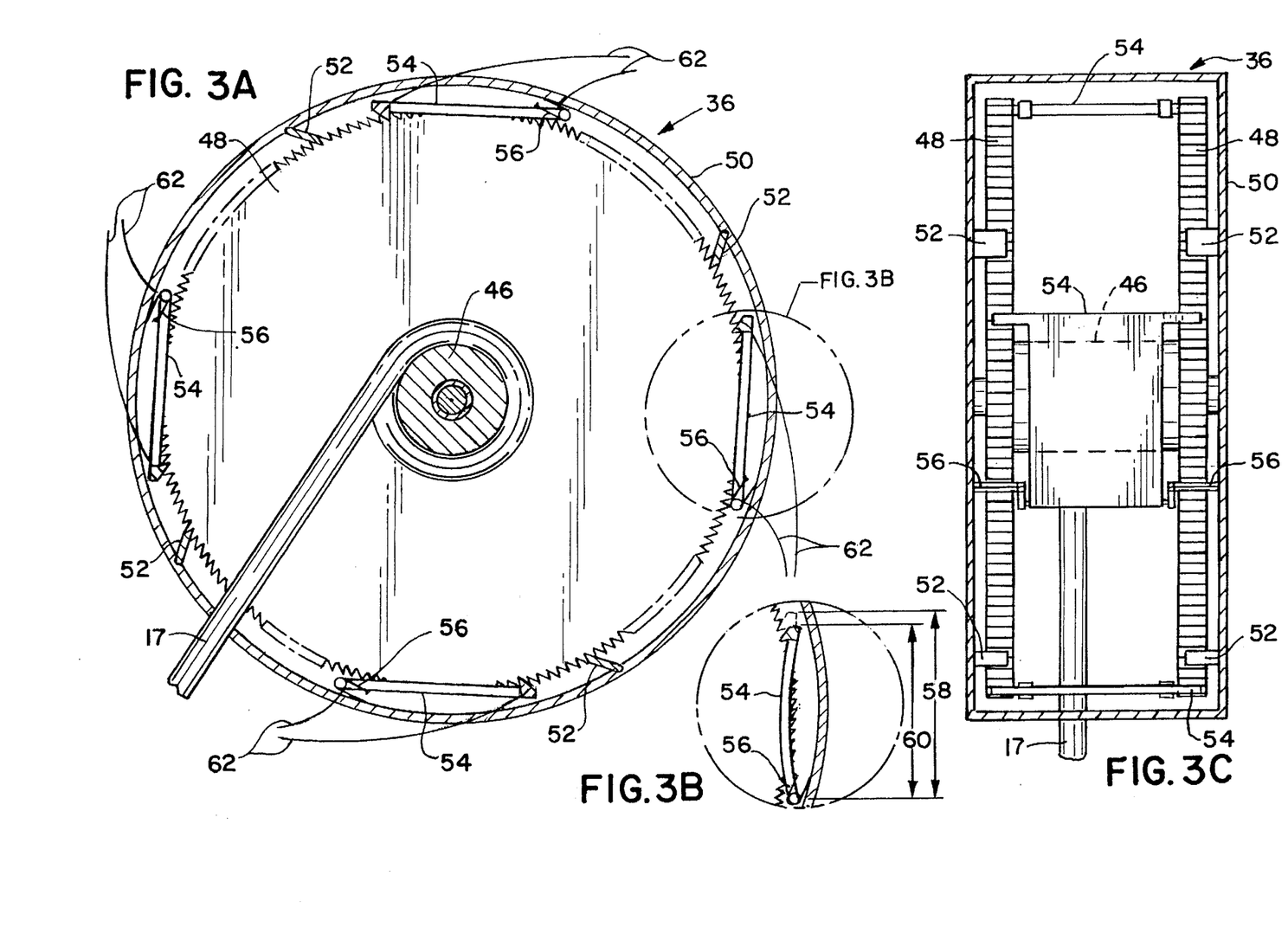
FIGS. 3A, 3B, and 3C illustrate top and side views of a thermally responsive actuator in accordance with the present invention.

With reference to FIGS. 3A, 3B, and 3C, one embodiment of the actuator 36 is shown. The actuator is fully implantable subcutaneously. The flexibility of sheath 15 and cable 17 allow the actuator to be positioned in any convenient location such as the abdominal region. The actuator 36 is responsive to and activated by a transcutaneous energy. The transcutaneous energy is radiated by the activation device 42 which is positioned over the actuator 36 without penetrating the patient's skin 44.

The cable 17 is connected to a take-up spool 46. Two sprockets 48 are securely attached on each side of the take-up spool 46 along a common axis. More or less sprockets may, of course, be used. When activated, the sprockets 48 rotate the take-up spool 46 which moves the cable 17. The cable movement in turn moves the bone segment 25.

The actuator 36 is enclosed in a casing 50 which includes one or more flexible or pivoted stops 52. One end of the stops 52 are secured to the inside of the casing 50 and the other end engages the teeth of the sprockets 48 to prohibit counter-rotation. One or more temperature sensitive arms 54 engage the teeth of the sprockets 48. Each arm 54 is supported on a pivot attached to the case 50, and maintained in contact with the sprocket by a torsion spring 56 or other like spring mechanisms. The arms 54 are constructed from a thermal alloy such as a shape memory metal. Alternately, bimetallic strips or other thermally responsive constructions are used to form the arms. At body temperature, the arms 54 have a first length 58. The arms 54 are activated by an increase in temperature generated from the transcutaneous energy source 42 positioned over the intact skin layer 44. In the preferred embodiment, the energy source 42 generates microwaves at a predetermined frequency which heats the arms 54. Alternately, other signals can be used to activate the arms 54 such as radiowaves, ultrasound, and others as known to those of ordinary skill in the art.

As the temperature increases, the temperature sensitive arms 54 shorten to a length 60, causing the sprockets 48 to rotate as shown in FIG. 3B. Each time the sprockets 48 rotate one tooth-length, the stops 52 engage the sprocket 48 at a new position. The arms 54 rotate the sprockets 48 approximately 2° per activation, although a greater or lesser amount of rotation can be performed by altering the length of the arms 54 and/or their temperature sensitivity. Once the transcutaneous energy is removed, the arms 54 return to a body temperature level and return to their initial length 58, ready for the next activation. The rotation of the sprockets 48 is incremental in the preferred embodiment, and alternatively is continuous.

As the sprockets 48 turn, the cable 17 is pulled and winds around the take-up spool 46, creating a tension force. The tension force pulls the bone segment 25 toward the first end 12 of femur 11. The non-compressible sheath 15 maintains the distance between the femur 11 and the actuator by a counter-compression force.

The activation system 42 includes an external energy source which is transcutaneously coupled to the actuator 36 through the intact skin layer 44. In the preferred embodiment, the external energy source includes a radio frequency electrical field generating coil (not shown). A wire coil is wrapped around the outside diameter of the actuator 36 and functions as an antenna receiving electrical current from the energy source 42. This current passes through wires 62 to the one or more thermally sensitive elements 54, warming them via resistive heating. A high frequency voltage applied to the field generating coil of the energy source 42 induces a similar high frequency current in the wire coil of the actuator 36. Alternately, the current in the receiving antenna is used to power other force or displacement producing systems, such as a motor, solenoid, or piezo-electric crystal.

In an alternative embodiment, the actuator 36 and sheath 15 are treated to inhibit tissue adhesion and to inhibit bacterial colonization as known by those of ordinary skill in the art. A force or motion measuring device (not shown) is attached to the cable 17 for detecting motion of the bone segment 25 by measuring displacement of the cable relative to the sheath. The motion measuring device is a transducer responding to tension in the cable 17. Alternately, the transducer is attached to the bone 11, the sheath 15, the actuator 36, or the external activator 42. Either or both force and motion may be sensed, using any one or a combination of strain gauge capacitative, inductive, or other instrumentation techniques known by those of ordinary skill in the art. Optionally, the actuator 36 is equipped with a monitor (not shown) to provide feedback signals indicating the conditions of the system. A signal transmitter (not shown) transmits the feedback signals outside the patient's body by telemetry, microwaves, and the like to a monitoring device. The actuator may also include a seal around the actuator interior to restrict fluid communication between the actuator and the patient's body.

Figure 4A:
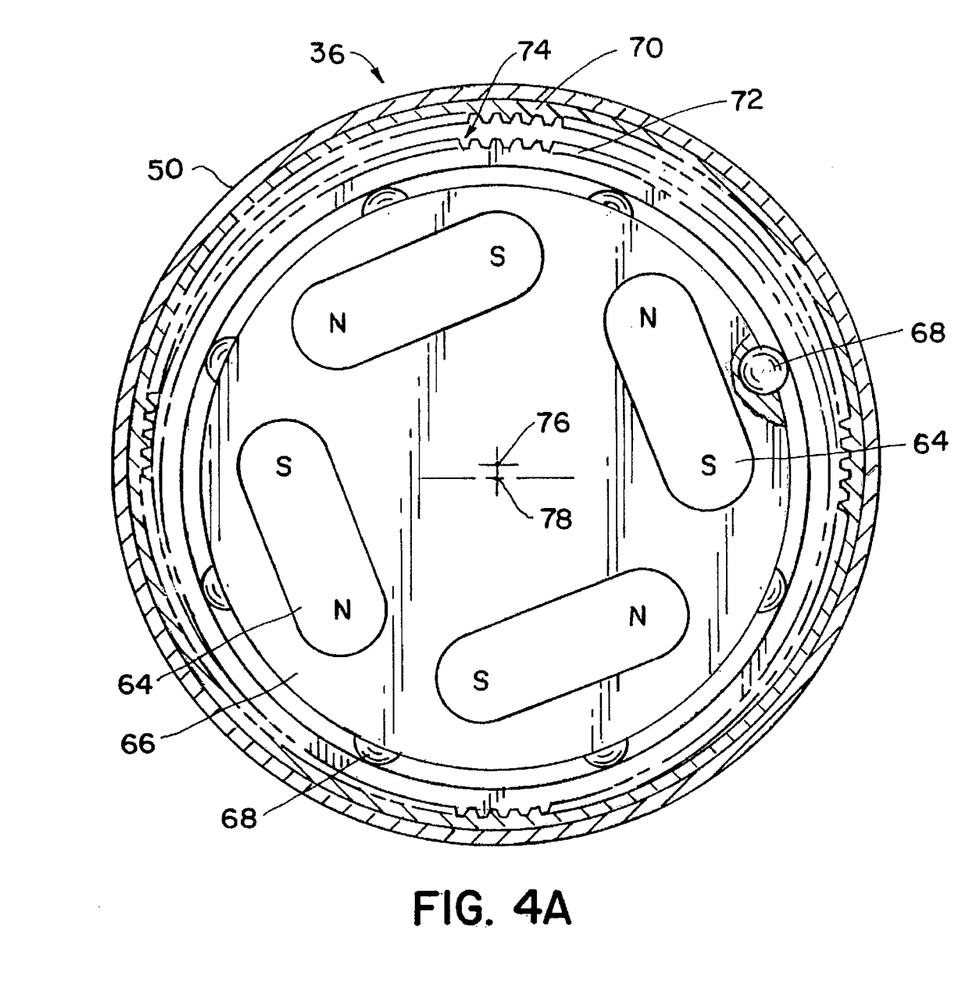
FIGS. 4A and 4B illustrate top and side views of a magnetically responsive actuator in accordance with the present invention; and, FIGS. 5A and 5B are a perspective schematic view of an embodiment of the invention configured for bone lengthening.
Figure 4B:
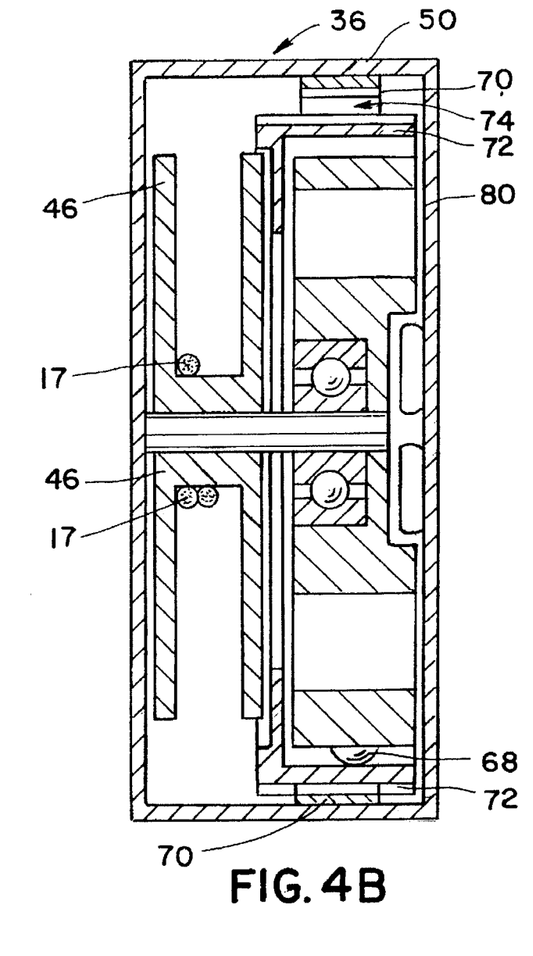

With reference to FIGS. 4A and 4B, another embodiment of the actuator 36 is shown. The actuator 36 includes a plurality of magnetically sensitive elements 64 such as magnets or magnetically soft materials, including ferrites, steel, high cobalt alloys, or compositions of similar performance. The magnetically sensitive elements 64 are positioned on a surface 66 supported by a set of anti-friction balls 68. The surface 66 is connected to a gear assembly including a ring gear 70 and a pinion 72. In the preferred embodiment, the gear assembly is a planocentric assembly. The pinion 72 has a fewer number of teeth and a smaller diameter than the ring gear 70 which creates a disengaged portion 74. During rotation, the pinion 72 wobbles. The surface 66 and the ring gear 70 are positioned along a common center-of-rotation 76. The actuator 36 is enclosed in a case 50. Alternatively, other types of gear assemblies can be used as known by those of ordinary skill in the art.

A take-up spool 46 is connected to the gear assembly. Rotation of the gear assembly rotates the take-up spool 46. The cable 17 is connected to the take-up spool and winds around the take-up spool 46 when the gear assembly rotates. Winding of the cable 17 produces a tension force axially along the cable and pulls the bone segment 25.

In this embodiment, the external energy source 42 is magnetically coupled to the actuator 36 at a center of magnetic coupling 78 over the intact layer of skin 44. The external energy source 42 includes a means for producing a magnetic field which include permanent magnets, electromagnets, coils, or other devices known by those of ordinary skill in the art. By rotating the external energy source 42, the magnetic field is rotated which activates the magnetically sensitive elements 64 of the actuator 36 causing the magnetically sensitive elements 64 to rotate. The rotation motion turns the take-up spool 46 and produces the tension force on the cable 17. When the magnetic field is removed from the actuator 36, the rotating assembly rests on a frictional surface 80 which prevents further rotation. When the magnetic field is again applied, the rotation assembly is lifted from the frictional surface 80 and spins on the anti-friction balls 68. In this manner, the bone segment 25 can be pushed as well by using the compression force applied by sheath 15. Between the activations, the external energy source can be optionally replaced by a foam pad (not shown). The foam pad is seeded with magnetically soft particles to short circuit the magnetic field radiated by the magnetic elements within the actuator 36, and to limit the approach of iron articles in the environment.

Alternatively, the actuator 36 includes a linkage or oscillating mechanism. The mechanism cyclically grips, unlocks, moves, relocks and releases the cable. The actuator 36 is magnetically, thermally, or electrically powered.

Figure 5A:
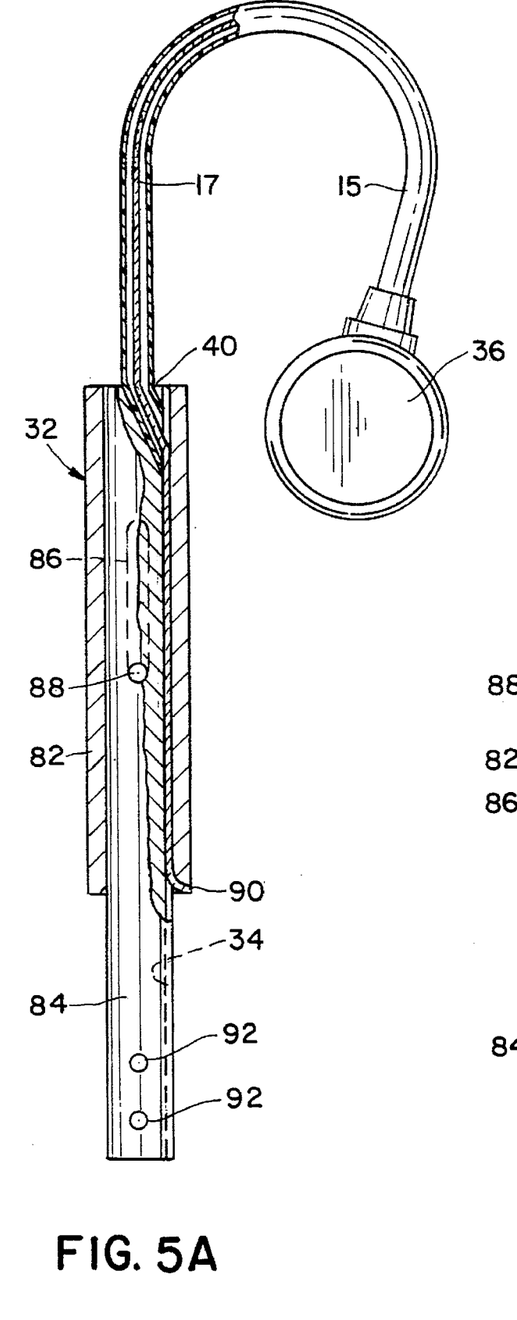

With reference to FIG. 5A, an alternative embodiment of the bone lengthening apparatus is provided. The rod 32 includes an outer rod 82 which slidably receives an inner rod 84. The inner rod 84 defines a slot 86 which receives a traverse anti-rotation bolt 88. After surgical insertion of the rod 32, the anti-rotation bolt 88 is placed through the first bone segment 12 fixing the outer rod 82 to the first bone segment 12. The anti-rotation bolt 88 fixes the rotation between the outer rod 82 and the inner rod 84, but allows axial advancement of the inner rod 84 within the outer rod 82.

The sheath 15 is secured to the inner rod 84 at point 40. The flexible cable 17 extends into the inner rod 84 along the slot 34. The flexible cable 17 is fixed to the outer rod 82 at point 90. The second end of the inner rod 84 defines one or more digital interlocking holes 92 for receiving a securing element such as a screw to secure the inner rod to the patient's bone.

Figure 5B:
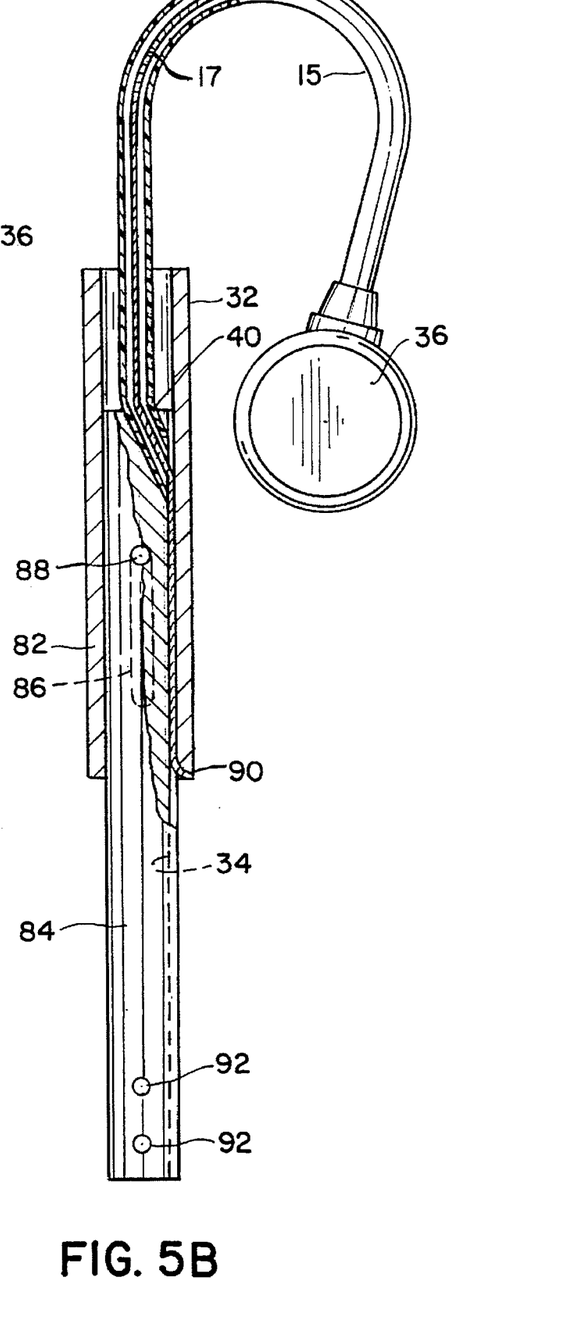

With reference to FIG. 5B, the rod 32 is shown after a period of distraction lengthening. When the actuator 36 is activated, the flexible cable 17 is incrementally pulled through the sheath 15. The outer rod 82 moves axially along the inner rod 84 as the cable 17 moves. The incremental movement of the outer rod 82 caused by tension from the cable 17 in turn separates the first bone segment 12 from second bone segment 13. The femur 11 is thus incrementally lengthened.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A surgically implantable cable apparatus for postoperative, gradual in vivo bone transport of a first bone segment between a second bone segment and a third bone segment comprising:

a means for securing the second bone segment and the third bone segment a fixed distance from one another;

a flexible cable having a first end portion for attaching to the first bone segment, and a second end portion;

an implantable prosthetic flexible, non-compressible sheath having a bore for accepting the cable, the sheath having a first end, a second end, and a means for securing the first end to the second bone segment, the sheath being adapted to transmit a counter-compression force to the second bone segment;

an implantable actuator connected to the second end portion of the flexible cable and to the second end of the sheath, and in response to a transcutaneous energy signal, the implantable actuator moves the flexible cable relative to the sheath; and, an energy source for generating the transcutaneous energy signal, the transcutaneous energy signal being capable of activating the implantable actuator through an intact skin layer.

2. The surgically implantable cable apparatus as set forth in claim 1 wherein the means for securing the second bone segment and the third bone segment includes an intramedullary rod having a locking element in each of the second bone segment and the third bone segment.

3. The surgically implantable cable apparatus as set forth in claim 2 wherein the locking element includes a transverse bone screw.

4. The surgically implantable cable apparatus as set forth in claim 1 wherein the implantable actuator includes a tensioning assembly connected to the second end portion of the flexible cable for applying tension to the flexible cable.

5. The surgically implantable cable apparatus as set forth in claim 4 wherein the tensioning assembly includes a cable take-up spool, the second end portion of the flexible cable being connected to the cable take-up spool.

6. The surgically implantable cable apparatus as set forth in claim 1 wherein the implantable actuator includes a means for selectively restricting motion of the flexible cable.

7. The surgically implantable cable apparatus as set forth in claim 1 wherein the implantable actuator includes a gear stage for moving the flexible cable relative to the sheath.

8. The surgically implantable cable apparatus as set forth in claim 7 wherein the gear stage has a planocentric configuration.

9. The surgically implantable cable apparatus as set forth in claim 1 wherein the implantable actuator includes a racheting means for moving the flexible cable relative to the sheath.

10. The surgically implantable cable apparatus as set forth in claim 1 wherein the actuator includes magnetically sensitive elements; and wherein the energy source includes means for generating a magnetic field as the transcutaneous energy signal.

11. The surgically implantable cable apparatus as set forth in claim 10 wherein the magnetically sensitive elements include magnets, and wherein the means for generating a magnetic field include magnets.

12. The surgically implantable cable apparatus as set forth in claim 10 wherein the implantable actuator includes a gear stage connected between the magnetically sensitive elements and the cable.

13. The surgically implantable cable apparatus as set forth in claim 10 further including a means to limit the acceleration of the magnetically sensitive elements as the energy source and the magnetically sensitive elements are approximated to each other.

14. The surgically implantable cable apparatus as set forth in claim 13 wherein the means to limit acceleration includes one of a damper, a cam, and a screw mechanism.

15. The surgically implantable cable apparatus as set forth in claim 1 wherein the actuator is electrically powered; and, the energy source includes means for transcutaneously activating the electrically powered actuator.

16. The surgically implantable cable apparatus as set forth in claim 15 wherein the implantable actuator further includes a receiving coil electrically connected to cable driving elements, the receiving coil generating a current in response to an external field from the energy source.

17. The surgically implantable cable apparatus as set forth in claim 1 wherein the implantable actuator includes thermally sensitive elements; and, wherein the energy source includes means for heating the thermally sensitive elements.

18. The surgically implantable cable apparatus as set forth in claim 17 wherein the thermally sensitive elements are made from a shape memory alloy, the thermally sensitive elements having a shape which changes as the transcutaneous energy signal from the energy source heats the temperature sensitive elements, the shape change moving the cable relative to the sheath.

19. The surgically implantable cable apparatus as set forth in claim 17 wherein the implantable actuator further includes a receiving coil electrically connected to the thermally sensitive elements, the receiving coil generating a current in response to an external field from the energy source.

20. The surgically implantable cable apparatus as set forth in claim 19 wherein the energy source includes an external coil, and during activation of in vivo bone transport, the external coil generating an electric field when activated and is positioned over the receiving coil separated by the intact skin layer.

21. The surgically implantable cable apparatus as set forth in claim 1 further including a means for detecting motion of the bone segment.

22. The surgically implantable cable apparatus as set forth in claim 21 wherein the means for detecting motion includes a transducer responsive to motion of the flexible cable.

23. The surgically implantable cable apparatus as set forth in claim 1 further including a means for measuring force applied to the bone segment.

24. The surgically implantable cable apparatus as set forth in claim 1 further including a sheath seal for reducing fluid communication to an interior of the sheath.

25. The surgically implantable cable apparatus as set forth in claim 1 further including an actuator seal for reducing fluid communication to an interior of the implantable actuator.

26. A surgically implantable apparatus for in vivo production of relative motion between a plurality of bone segments of a bone, comprising:
 an implanted actuator for producing a force, the actuator being remotely located relative to the bone incorporating the plurality of bone segments;
 means for energizing said actuator, while maintaining the skin layer intact; and,
 means for transmitting the force from the actuator to the bone including a flexible, non-compressible sheath.

27. The surgically implanted apparatus as set forth in claim 26 wherein the means for transmitting the force includes a flexible cable being slidably received axially through the flexible, non-compressible sheath, the flexible cable having a first end portion attached to one of the plurality of bone segments, and a second end portion attached to the actuator.

28. The surgically implantable apparatus as set forth in claim 27 wherein the flexible, non-compressible sheath includes a first end with means for securing the flexible, non-compressible sheath to the bone, and a second end portion for attaching to the actuator, the sheath being adapted to transmit a counter-force between the bone and the actuator.

29. The surgically implantable apparatus as set forth in claim 27 wherein the flexible cable is adapted to transmit force along its length.

30. The surgically implantable apparatus as set forth in claim 27 wherein the implanted actuator includes a force multiplying means connected to the flexible cable for moving the flexible cable relative to the flexible, non-compressible sheath.

31. The surgically implantable apparatus as set forth in claim 30 wherein the force multiplying means is a gear stage.

32. The surgically implantable apparatus as set forth in claim 26, the means for energizing the actuator including an implanted power source connected to the actuator by a switch, the switch being responsive to a transcutaneous signal.

33. The surgically implantable apparatus as set forth in claim 26, the means for energizing the actuator including means external to the skin for radiating energy, and means under the skin for receiving the energy and conducting the energy to the actuator.

34. The surgically implantable apparatus as set forth in claim 33, further including an external transmitting antenna for producing an electric field in response to a high frequency electrical current, and an internal antenna outputting an electrical current induced by the radiated electrical field.

35. The surgically implantable apparatus as set forth in claim 26 wherein the actuator includes a set of magnetically sensitive elements, responsive to a magnetic field produced outside the body.

36. The surgically implantable apparatus as set forth in claim 26 further including a means for defining an initial positional relationship between the plurality of bone segments of the bone.

37. The surgically implantable apparatus as set forth in claim 36 wherein the means for defining an initial positional relationship includes an intramedullary rod.

38. The surgically implantable apparatus as set forth in claim 26 further including a means for defining a fixed positional relationship between a plurality of bone segments of the bone.

39. The surgically implantable apparatus as set forth in claim 26 wherein the implanted actuator is electrically powered.

40. The surgically implantable apparatus as set forth in claim 26 wherein the implanted actuator includes thermally sensitive elements for producing motion in response to a change in temperature.

41. The surgically implantable apparatus as set forth in claim 26 further including a transducer for monitoring a system status of the surgically implantable apparatus.

42. The surgically implantable apparatus as set forth in claim 26 further including a transducer for measuring the force produced by the implanted actuator.

43. The surgically implantable apparatus as set forth in claim 26 further including a transducer for measuring a displacement of the plurality of bone segments.

44. A surgically implantable apparatus for in vivo displacement of a bone segment, comprising:
 a flexible cable having a first end portion with means for attaching the cable to the bone segment to which a motion is applied;
 an implantable, flexible, non-compressible sheath having a bore for accepting the cable;
 an implanted, remotely located actuator for moving the bone segment by pulling the cable through the sheath; and,
 means for activating the actuator while maintaining an intact skin layer.

45. The surgically implantable apparatus as set forth in claim 44 further including a means to establish a positional relationship of a plurality of bone segments in at least one dimension.

46. The surgically implantable apparatus as set forth in claim 44 wherein the flexible cable is adapted to transmit force along its length.

47. The surgically implantable apparatus as set forth in claim 44 further including a means for providing a feedback signal indicating a system operation.

48. The surgically implantable apparatus as set forth in claim 47 further including a telemetry means for delivering the feedback signal outside of the patient.

49. A method for surgically treating by distraction a selected bone of a patient, comprising the steps of:
 affixing an implant to the selected bone;
 severing the selected bone into a plurality of bone segments;
 affixing the implant to the plurality of bone segments;
 gradually moving at least one bone segment of the plurality of bone segments relative to one another a selected dimension per unit of time in response to a transcutaneous energy signal; and, wherein in the step of gradually moving, a flexible force transmitting member extends from the implant to a remote site where force is applied thereto.

50. The method as set forth in claim 49 wherein the remote site is subcutaneous within the patient.

51. The method as set forth in claim 49 wherein in the step of affixing the implant to the selected bone, the implant is placed in an intramedullary canal of the selected bone.

52. The method as set forth in claim 49 wherein the gradually moving step includes rotating a force transmitting member to move the at least one bone segment.

53. The method as set forth in claim 49 further including, before the gradually moving step, inserting a flexible cable axially through the flexible force transmitting member; and fixing the flexible cable to the selected bone.

54. The method as set forth in claim 49 wherein the gradually moving step includes transporting the at least one bone segment across an intermediate gap between ends of the selected bone.

55. The method as set forth in claim 49 wherein the gradually moving step includes producing relative motion between ends of the selected bone.

56. A surgically implantable cable apparatus for in vivo bone displacement of a first bone segment that is spaced from a second bone segment comprising:

a) a flexible cable having first and second end portions, the first end portion including means for attaching the cable to the first bone segment to which force is to be applied;

b) an implantable prosthetic flexible, non-compressible sheath having a bore for accepting the cable, and through which a counter-compression force is transmitted to the second bone segment, the sheath having a first end and second end;

c) means for mechanically linking the first end of the sheath and the second bone segment; and d) a subcutaneous actuator, attached to the second end of the sheath and the second end portion of the cable, for moving the cable through the sheath to move the first and second bone segments relative to each other over a period of time after surgical implantation when the cable is manipulated to move within the sheath in response to a transcutaneous signal.

* * * * *